United States Patent
Takeuchi et al.

(10) Patent No.: US 11,759,171 B2
(45) Date of Patent: Sep. 19, 2023

(54) ULTRASONIC PROBE AND MANUFACTURING METHOD THEREOF

(71) Applicant: CANON MEDICAL SYSTEMS CORPORATION, Otawara (JP)

(72) Inventors: Takashi Takeuchi, Otawara (JP); Shohei Sasaki, Otawara (JP); Hiroyuki Shikata, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/386,171

(22) Filed: Jul. 27, 2021

(65) Prior Publication Data
US 2022/0031284 A1    Feb. 3, 2022

(30) Foreign Application Priority Data
Jul. 29, 2020   (JP) .................................. 2020-128073

(51) Int. Cl.
  *A61B 8/00*  (2006.01)
  *B06B 1/06*  (2006.01)
  *H10N 30/088*  (2023.01)

(52) U.S. Cl.
  CPC .......... *A61B 8/4444* (2013.01); *A61B 8/4494* (2013.01); *B06B 1/0622* (2013.01); *H10N 30/088* (2023.02)

(58) Field of Classification Search
  CPC ... A61B 8/4444; A61B 8/4494; B06B 1/0622; B06B 1/0629; H10N 30/088
  See application file for complete search history.

(56) References Cited

U.S. PATENT DOCUMENTS

| | | | |
|---|---|---|---|
| 5,920,523 A * | 7/1999 | Hanafy | B06B 1/0629 29/25.35 |
| 2006/0119222 A1* | 6/2006 | Sato | A61B 8/4494 310/334 |
| 2013/0286786 A1* | 10/2013 | Yoshida | A61B 8/4494 367/140 |
| 2014/0288430 A1 | 9/2014 | Uchibori | |
| 2017/0288638 A1* | 10/2017 | Wildes | H10N 30/08 |
| 2019/0305209 A1* | 10/2019 | Tada | H10N 30/082 |
| 2021/0015458 A1* | 1/2021 | Kitamura | A61B 8/12 |

FOREIGN PATENT DOCUMENTS

JP   2000125394 A  *  4/2000
JP     5924298 B2     5/2016

* cited by examiner

*Primary Examiner* — Colin T. Sakamoto
*Assistant Examiner* — Tommy T Ly
(74) *Attorney, Agent, or Firm* — Oblon, McClelland, Maier & Neustadt, L.L.P.

(57) ABSTRACT

An ultrasonic probe of an embodiment includes a vibrator, an acoustic matching layer, and a back layer. The vibrator includes a plurality of vibrating elements arranged in a first direction. The acoustic matching layer is formed on a living body side of the vibrator. The back layer is formed on a back side of the vibrator opposite the living body side. The plurality of vibrating elements are formed by being divided by first grooves passing through the vibrator and the back layer. Second grooves passing through the vibrating elements and penetrating into the back layer are provided in each of the vibrating elements. A penetration depth of the second grooves in a second direction in the back layer is less than a width of the second grooves in the first direction in the vibrating elements.

6 Claims, 8 Drawing Sheets

ULTRASONIC PROBE AND MANUFACTURING METHOD THEREOF

CROSS-REFERENCE TO RELATED APPLICATION

The present application claims priority based on Japanese Patent Application No. 2020-128073 filed Jul. 29, 2020, the content of which is incorporated herein by reference.

FIELD

Embodiments disclosed in the present description and drawings relate to an ultrasonic probe and a manufacturing method thereof.

BACKGROUND

An acoustic unit of an ultrasonic probe includes, for example, a vibrator, an acoustic matching layer provided on a living body side of the vibrator, and a back layer provided on the back side of the vibrator. Although a piezoelectric element serving as the vibrator is divided into, for example, vibrating elements (main dice) by a plurality of first grooves (main dice grooves) provided in spacings of channels connected through electrical wiring, a transverse vibration mode is intensified when the pitch of the vibrating elements is wide. To suppress the transverse vibration mode, a technology in the related art for dividing the main dice into sub-dice by providing a second groove (sub-dice groove) in each vibrating element and the back layer is known.

However, the back layer has a high acoustic impedance and thus a dicing property is low in many cases. Accordingly, when the second groove is provided in the back layer, there are some cases where the damage of the back layer occurs. Particularly, in the case of a vibrator with multiple channels such as a two-dimensional array, the influence caused by provision of second grooves in a back layer is likely to become serious because the number of vibrating elements increases and thus the number of second grooves also increases.

DETAILED DESCRIPTION

Hereinafter, embodiments of ultrasonic probes and a manufacturing method thereof will be described with reference to the drawings.

An ultrasonic probe of an embodiment includes a vibrator, an acoustic matching layer, and a back layer. The vibrator includes a plurality of vibrating elements arranged in a first direction. The acoustic matching layer is formed on a living body side of the vibrator. The back layer is formed on a back side of the vibrator opposite the living body side. The plurality of vibrating elements are formed by being divided by first grooves passing through the vibrator and the back layer. Second grooves passing through the vibrating elements and penetrating into the back layer are provided in each of the vibrating elements. A penetration depth of the second grooves in a second direction in the back layer is less than a width of the second grooves in the first direction in the vibrating elements.

First Embodiment

Figure 1:
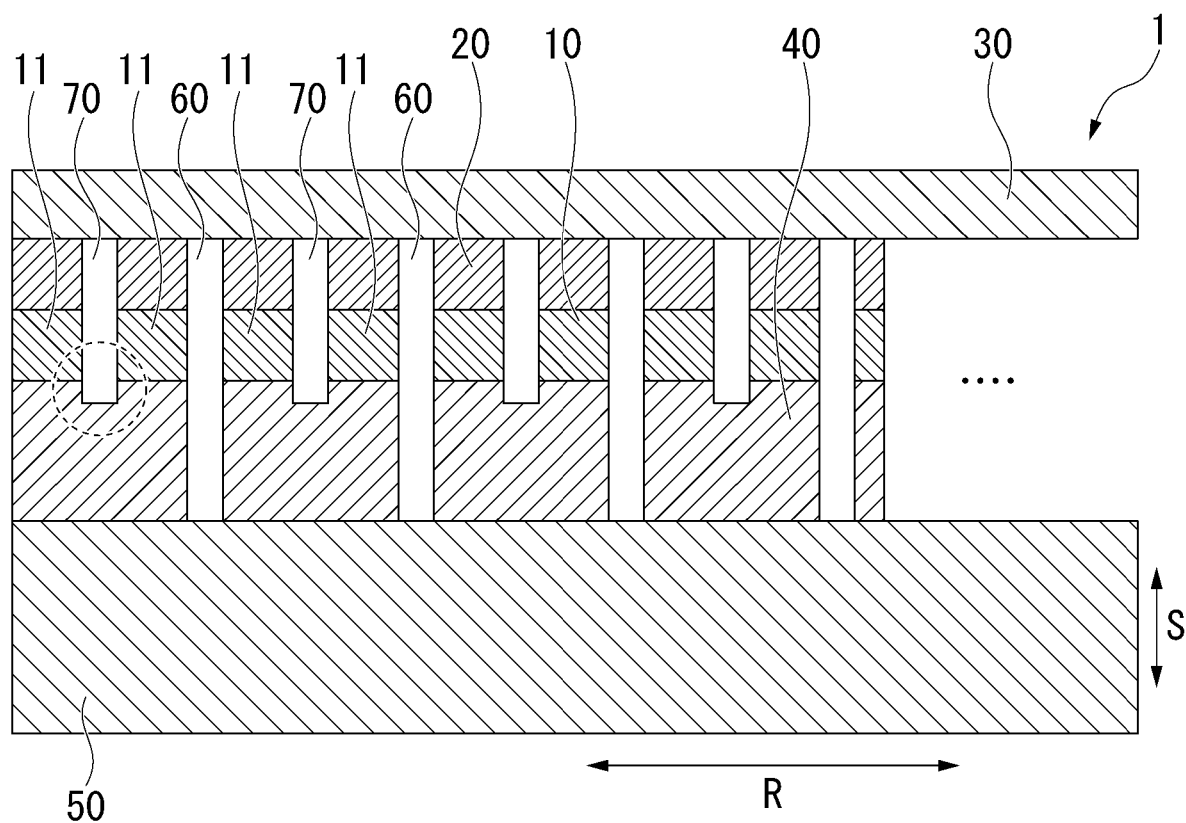
FIG. 1 is a cross-sectional view of an ultrasonic probe 1 of a first embodiment.

An ultrasonic probe 1 of a first embodiment will be described. FIG. 1 is a cross-sectional view of the ultrasonic probe 1 of the first embodiment. The ultrasonic probe 1 includes, for example, a vibrator 10, an acoustic matching layer 20, a lens layer 30, a back layer 40, and a back material 50. The vibrator 10 includes, for example, a λ/4 piezoelectric body having a thickness of ¼ of a wavelength (λ) determined based on an ultrasonic propagation velocity.

The vibrator 10 includes a plurality of vibrating elements 11 arranged in a first direction R. The vibrating elements 11 are divided, for example, in units of electrical signal wires. The plurality of vibrating elements 11 are formed by being divided by first grooves 60 that pass through the vibrator 10. The first grooves 60 are provided at regular intervals in the first direction R. Accordingly, the vibrating elements 11 are arranged at regular intervals along the first direction R. The interval between the vibrating elements 11 is called a main pitch. The first direction R is a scanning direction defined as a direction in which the ultrasonic probe 1 is moved, for example, when diagnosis is performed using the ultrasonic probe 1.

Second grooves 70 that cut the vibrating elements 11 into sub-dice are provided in each of the plurality of vibrating elements 11. The second grooves 70 pass through the acoustic matching layer 20 and the vibrator 10 and penetrate (enter) into the back layer 40 to a middle depth thereof. In the following description, one vibrating element may be referred to as main dice and vibrating elements obtained by dividing the main dice by the second grooves 70 may be referred to as sub-dice.

To eliminate unnecessary vibration, the vibrating elements 11 are divided into an integer number of elements by the second grooves 70. The vibrating elements 11 divided by the first grooves 60 become main dice, and the main dice are divided by the second grooves 70 to become sub-dice. In the plurality of vibrating elements 11, sub-dice included in one main dice are grouped and connected to an electrical signal wire.

Figure 2:
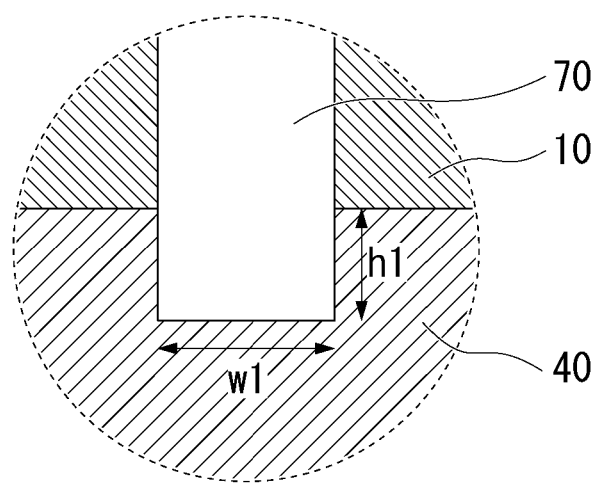
FIG. 2 is a partial enlarged view of FIG. 1.

As shown in FIG. 2, a penetration depth h1 in a second direction S that is a depth direction or the like of the second grooves 70 in the back layer 40 is less than a width w1 in the first direction R of the second grooves 70 in the vibrating elements 11. The penetration depth h1 of the second grooves 70 may be less than the width w1 of the second grooves 70, for example, 0.8 times or less, 0.5 times or less, or 0.3 times or less the width of the second grooves 70.

The acoustic matching layer 20 is provided on a living body side of the vibrator 10. The living body side is a side disposed on the side of a living body when ultrasonic waves are transmitted/received to/from a subject (living body) through the ultrasonic probe 1. The acoustic matching layer 20 is formed of two layers of a first acoustic matching layer and a second acoustic matching layer. The first acoustic matching layer and the second acoustic matching layer of the acoustic matching layer 20 have a thickness of ¼ of the wavelength (λ), for example. The matching layer may be formed as a single layer. The lens layer 30 is attached onto the acoustic matching layer 20 using an adhesive, for example. The lens layer 30 causes ultrasonic waves transmitted from the vibrator 10 to converge at a certain depth.

The back layer 40 is provided on the back side of the vibrator 10. The back side is a side opposite the living body side when viewed from the vibrator 10. The back layer 40 has a higher acoustic impedance than the vibrator 10. The back layer 40 is provided in order to attenuate mechanical vibrations of the vibrator 10. Transmission power of ultrasonic waves transmitted from the vibrator 10 to the living body side is increased by providing the back layer 40.

The back material 50 is provided on the back side of the back layer 40. The back material 50 is provided, for example, in order to attenuate acoustic vibrations of the vibrator 10. The back material 50 attenuates ultrasonic waves radiated from the vibrator 10 in the direction of the back material 50. The back material 50 also serves as a structural holding material of the vibrator 10.

Figure 3A:
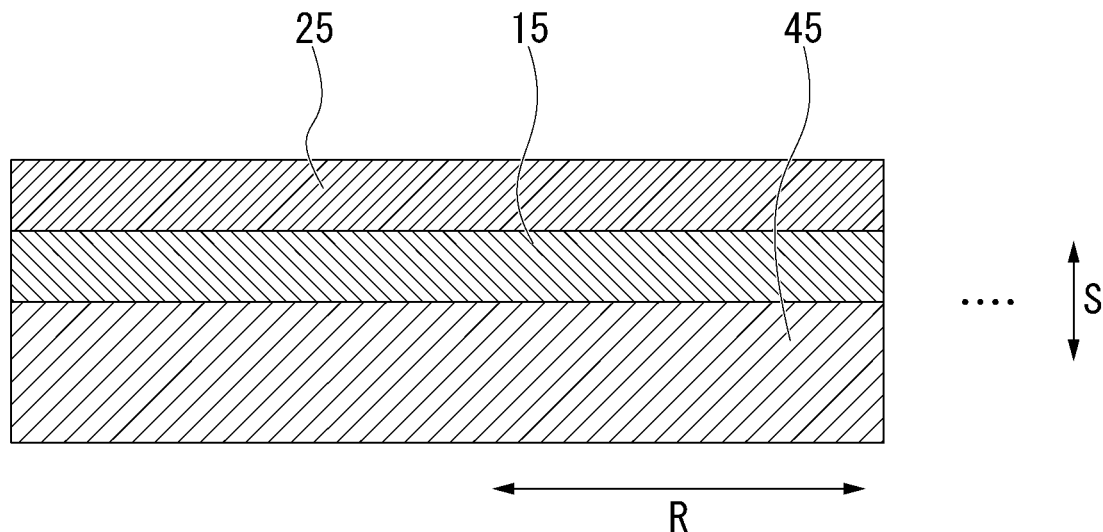
FIG. 3A is a diagram showing a manufacturing process of the ultrasonic probe 1.

Next, a manufacturing procedure of the ultrasonic probe 1 of the embodiment will be described. FIG. 3A to FIG. 3D are diagrams showing a manufacturing process of the ultrasonic probe 1. For example, a manufacturer who manufactures the ultrasonic probe 1 first provides, for example, an unprocessed plate-shaped back layer 45 which becomes the processed back layer 40, as shown in FIG. 3A. The manufacturer may be a human resource such as a worker, a mechanical resource such as a robot, or a combination thereof.

Subsequently, the manufacturer laminates, for example, an unprocessed plate-shaped vibrator 15 which becomes the processed vibrator 10 on the upper surface (the surface of one side of the unprocessed back layer 45). Subsequently, the manufacturer laminates, for example, an unprocessed plate-shaped acoustic matching layer 25 which becomes the processed acoustic matching layer 20 on the upper surface of the unprocessed vibrator 15 (the surface opposite the surface on which the unprocessed back layer 45 is provided).

Figure 3B:
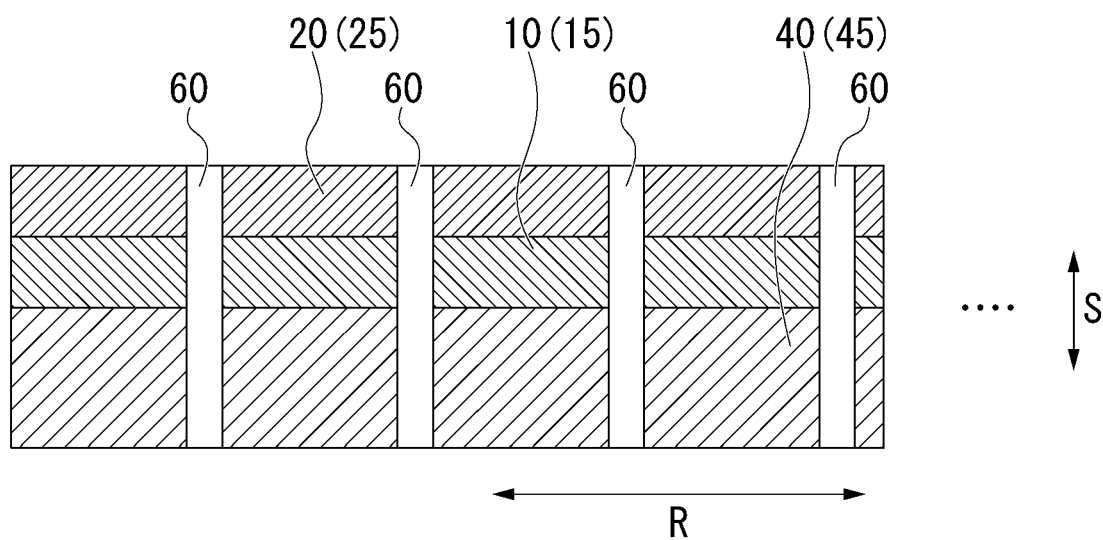
FIG. 3B is a diagram showing the manufacturing process of the ultrasonic probe 1.

Subsequently, the manufacturer performs dicing from the upper surface of the unprocessed acoustic matching layer 25 (the surface opposite the surface on which the unprocessed vibrator 15 is provided) to the unprocessed back layer 45 across the unprocessed acoustic matching layer 25 and the unprocessed vibrator 15 at a main dice pitch, for example, using a dicer. The manufacturer forms the vibrator 10 including a plurality of vibrating elements 11 by performing dicing to divide the unprocessed vibrator 15 by a plurality of first grooves 60 passing through the unprocessed vibrator 15 and the unprocessed back layer 45, as shown in FIG. 3B. The acoustic matching layer 20 and the back layer 40 that the first grooves 60 pass through are formed through dicing of the unprocessed acoustic matching layer 25 and the unprocessed back layer 45.

Figure 3C:
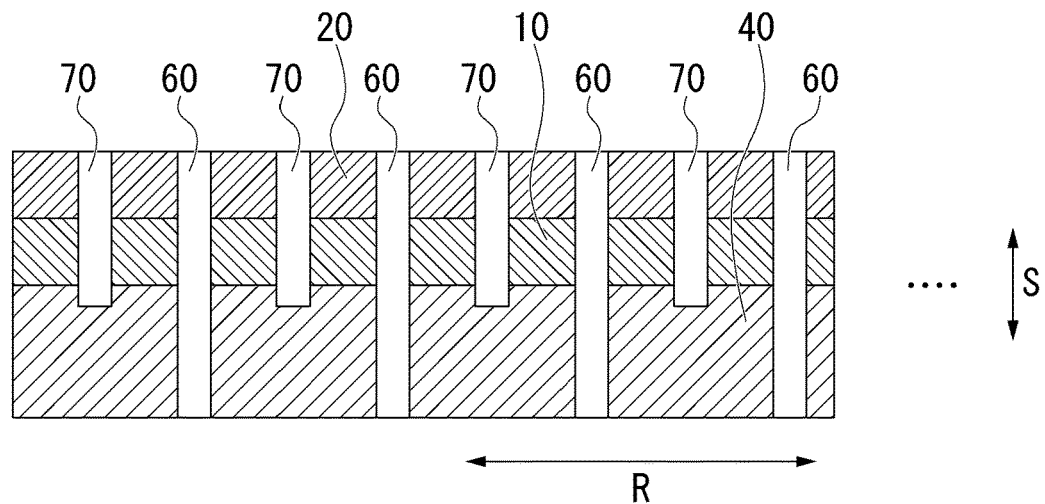
FIG. 3C is a diagram showing the manufacturing process of the ultrasonic probe 1.

Subsequently, the manufacturer performs dicing from the acoustic matching layer 20 laminated on the upper surface of the plurality of vibrating elements 11 to a middle position in the back layer 40 in the second direction S across the vibrating elements 11 at a sub-dice pitch, for example, using a dicer, as shown in FIG. 3C. The sub-dice pitch is ½ of the main dice pitch. The manufacturer forms second grooves 70 passing through the vibrating elements 11 and having a penetration depth in the second direction S in the back layer 40 which is less than a width in the first direction R by performing dicing. The penetration depth of the second grooves 70 can be adjusted by changing a depth of dicing.

Figure 3D:
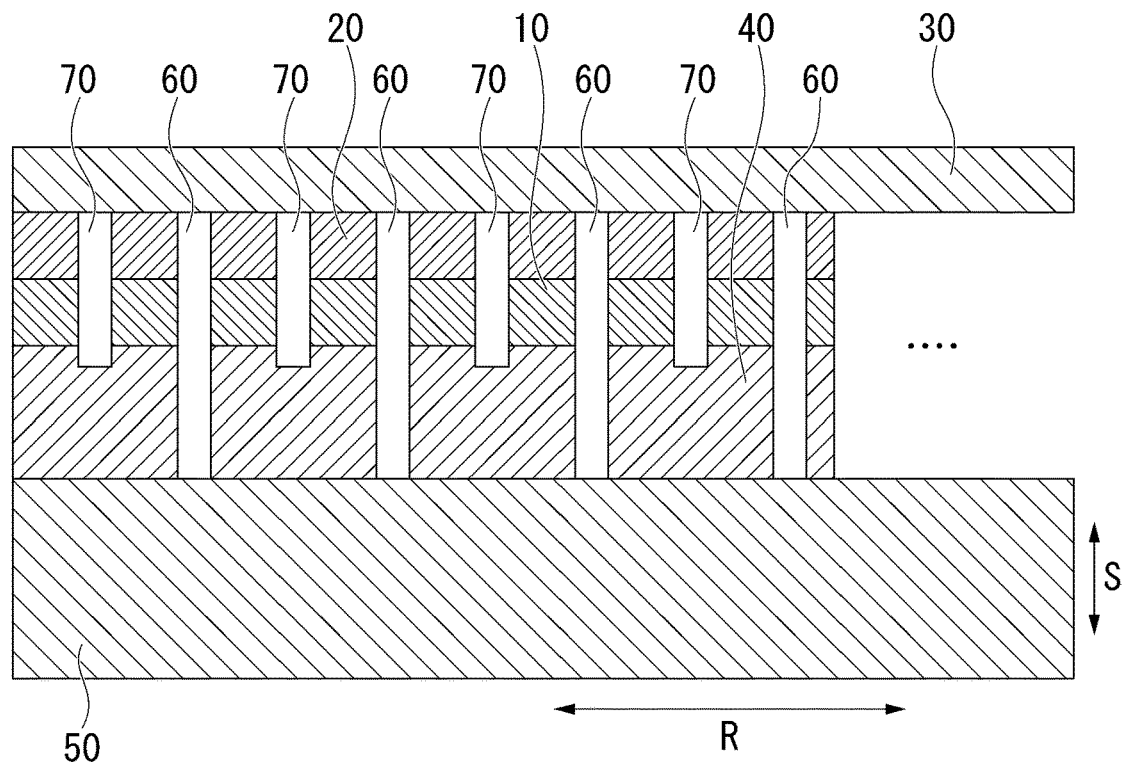
FIG. 3D is a diagram showing the manufacturing process of the ultrasonic probe 1.

Subsequently, the manufacturer forms the back material 50 on the back surface of the back layer 40, as shown in FIG. 3D. Further, the manufacturer forms the lens layer 30 on the upper surface of the acoustic matching layer 20. Through this procedure, the manufacturer manufactures the ultrasonic probe 1.

In the ultrasonic probe 1 of the first embodiment, the second grooves 70 passing through the vibrating elements 11 and penetrating into the back layer 40 are provided in the vibrator 10. Accordingly, a transverse vibration mode of the vibrator 10 can be suppressed. In the ultrasonic probe 1, the penetration depth of the second grooves 70 penetrating into the back layer 40 is less than the width of the second grooves 70 in the first direction R in the vibrator 10. Accordingly, it is possible to reduce damage to the back layer 40 by providing the second grooves 70.

Second Embodiment

Figure 4:
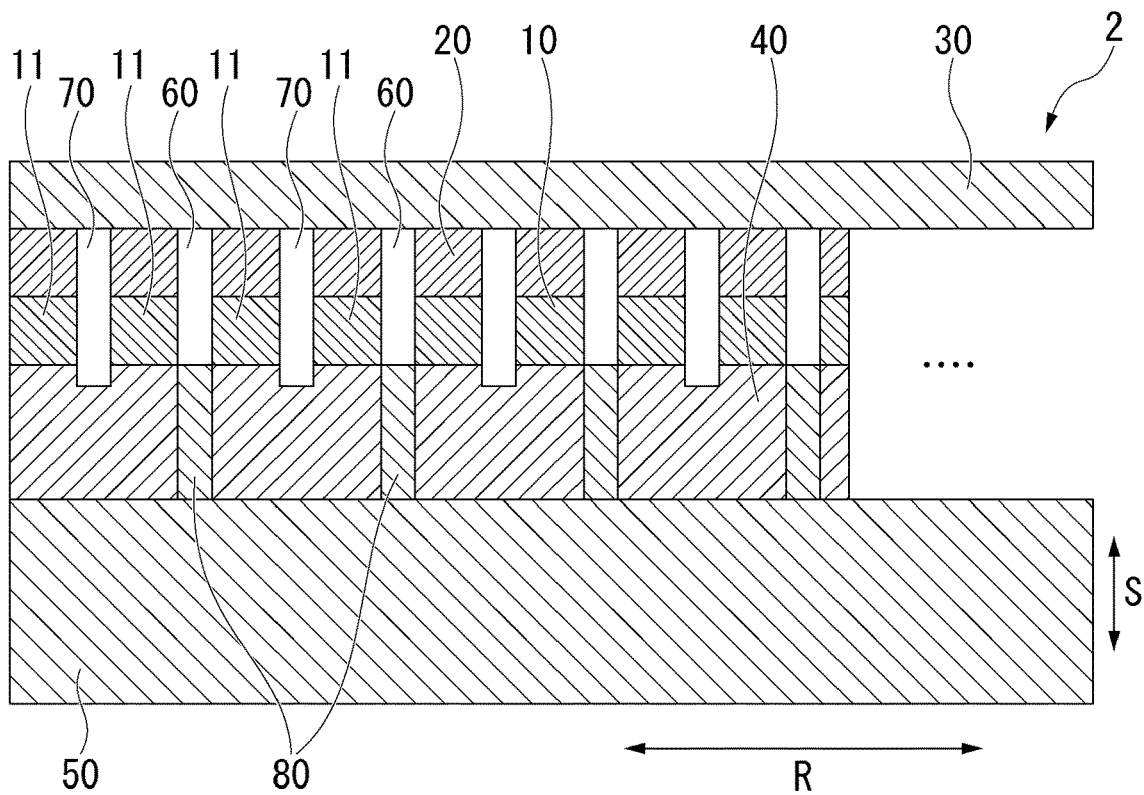
FIG. 4 is a cross-sectional view of an ultrasonic probe 2 of a second embodiment.

An ultrasonic probe 2 of a second embodiment will be described. FIG. 4 is a cross-sectional view of the ultrasonic probe 2 of the second embodiment. The ultrasonic probe 2 differs from the ultrasonic probe of the first embodiment in that a filler 80 is filled in the first grooves 60 formed in the back layer 40. Other components are the same as those of the ultrasonic probe 1 of the first embodiment.

The back layer 40 and the vibrator 10 of the ultrasonic probe 2 are attached using an adhesive, for example. This is also true of the ultrasonic probe 1 of the first embodiment. The adhesive is, for example, a liquid epoxy adhesive having an epoxy resin as a main ingredient. The filler 80 filled in the first grooves 60 provided in the back layer 40 is the epoxy resin used as the adhesive that has flowed into the first grooves 60 and solidified.

Next, a manufacturing procedure of the ultrasonic probe 2 of the second embodiment will be described focusing on differences from the first embodiment. At the time of manufacturing the ultrasonic probe 2, a manufacturer manufactures the unprocessed plate-shaped back layer 45 shown in FIG. 3A as in the ultrasonic probe 1. Subsequently, the manufacturer forms the unprocessed vibrator 15 on the upper surface of the unprocessed back layer 45 and coats the adhesive between the unprocessed back layer 45 and the unprocessed vibrator 15. Subsequently, the manufacturer presses the unprocessed back layer 45 with the unprocessed vibrator 15 before the adhesive solidifies to attach the unprocessed back layer 45 and the unprocessed vibrator 15 to each other. Subsequently, the manufacturer forms the unprocessed acoustic matching layer 25 on the upper surface of the unprocessed vibrator.

Subsequently, the manufacturer dices the unprocessed vibrator 15 and the unprocessed back layer before the adhesive solidifies. The manufacturer divides the unprocessed vibrator 15 by the plurality of first grooves 60 passing through the unprocessed vibrator 15 and the unprocessed back layer 45 to form the vibrator 10 including a plurality of vibrating elements 11 and form the acoustic matching layer 20 and the back layer 40 by performing dicing.

Further, the manufacturer presses the unprocessed back layer 45 with the unprocessed vibrator 15 at the time of forming the first grooves 60 such that the adhesive flows into the first grooves 60 in the back layer 40. Thereafter, the manufacturer fills the adhesive as a filler in the first grooves 60 in the back layer 40 by solidifying the adhesive that has flowed into the first grooves 60 in the back layer 40.

Subsequently, the manufacturer performs dicing of the plurality of vibrating elements 11 to form the second grooves 70 passing through the vibrating elements 11 and penetrating into the back layer 40. Thereafter, the manufacturer forms the back material 50 on the back surface of the back layer 40 and forms the lens layer 30 on the upper surface of the acoustic matching layer 20. Through this procedure, the manufacturer manufactures the ultrasonic probe 2.

The ultrasonic probe 2 of the second embodiment can suppress the transverse vibration mode of the vibrator 10 because the second grooves 70 are provided therein as in the first embodiment. Since the penetration depth of the second grooves 70 is less than the width of the second grooves 70 in the ultrasonic probe 2, it is possible to reduce damage to the back layer 40 by providing the second grooves 70. Since the filler 80 is filled in the first grooves 60 of the back layer 40 in the ultrasonic probe 2, it is possible to further reduce damage to the back layer 40. Further, manufacturing is facilitated because the adhesive coated between the unprocessed back layer 45 and the unprocessed vibrator 15 need not be finely adjusted.

Figure 5:
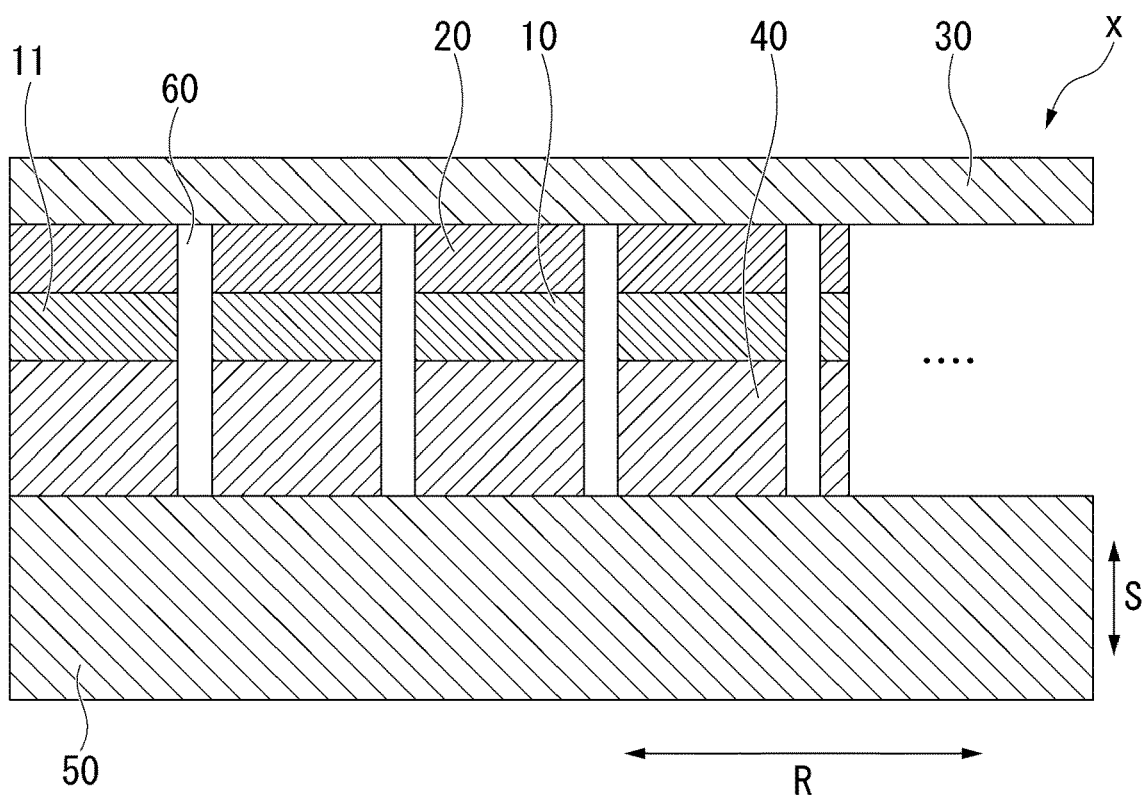
FIG. 5 is a cross-sectional view of an ultrasonic probe X in the related art.

Frequency response of the ultrasonic probe 1 of the first embodiment and the second ultrasonic probe 2 of the second embodiment will be described in comparison with an ultrasonic probe X in the related art. FIG. 5 is a cross-sectional view of the ultrasonic probe X in the related art. The effects of the ultrasonic probe 1 and the ultrasonic probe 2 will be described using the ultrasonic probe X in the related art shown in FIG. 5 as a comparison target. The ultrasonic probe X in the related art that is a comparison target does not include the second grooves 70 as compared to the ultrasonic probe 1. The ultrasonic probe X in the related art has a configuration in which a main dice is not divided into sub-dice. Other components are the same as those of the ultrasonic probe 1.

Figure 6:
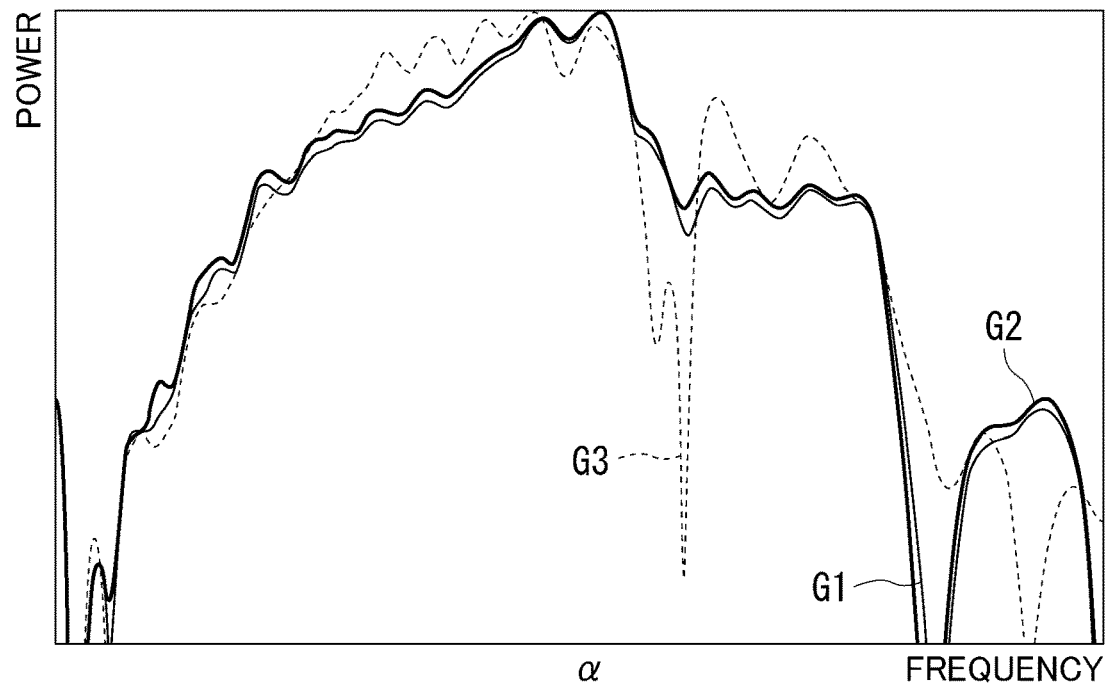
FIG. 6 is a graph showing a relationship between power and a frequency range of a vibrator.

FIG. 6 shows graphs of frequency responses of ultrasonic probes. A first graph G1 shows a frequency response of the ultrasonic probe 1, a second graph G2 shows a frequency response of the ultrasonic probe 2, and a third graph G3 shows a frequency response of the ultrasonic probe X. As can be seen in FIG. 6, a result in which a frequency band near a frequency $\alpha$ which falls in power is seen is obtained in the frequency response of the ultrasonic probe X in comparison with the frequency responses of the ultrasonic probes 1 and 2. This result shows that the ultrasonic probes 1 and 2 of the embodiments have frequency responses superior to that of the ultrasonic probe X in the related art.

Third Embodiment

Figure 7:
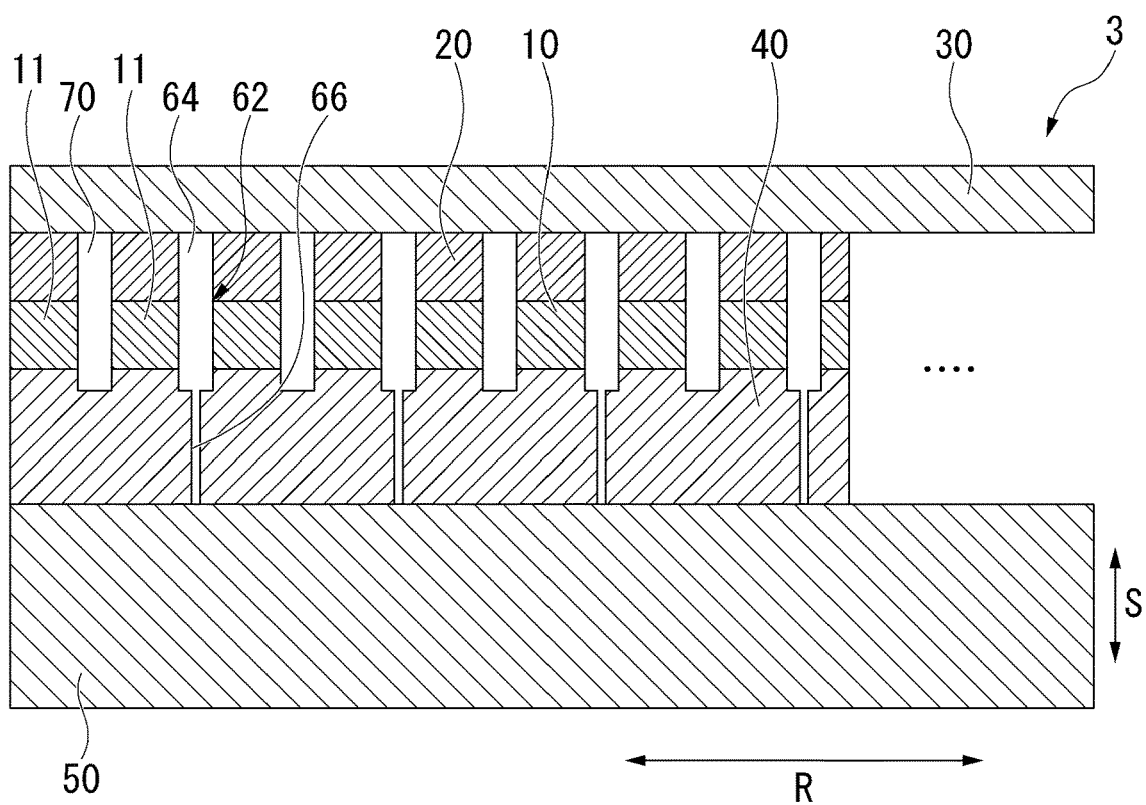
FIG. 7 is a cross-sectional view of an ultrasonic probe 3 of a third embodiment.

An ultrasonic probe 3 of a third embodiment will be described. FIG. 7 is a cross-sectional view of the ultrasonic probe 3 of the third embodiment. The ultrasonic probe 3 differs from the ultrasonic probe 1 of the first embodiment in that stepped first grooves 62 are provided instead of the first grooves 60 provided in the ultrasonic probe 1 of the first embodiment. Each stepped first groove 62 includes a dividing first groove 64 that divides the vibrator 10 and a narrow first groove 66 that is formed in the back layer 40 in connection with the stepped first groove 62 and has a narrower width than the dividing first groove 64.

The dividing first groove 64 passes through the vibrator 10 and a part thereof penetrates into the back layer 40. The penetration depth of the dividing first groove 64 in the back layer 40 is the same as the penetration depth of the second groove 70 in the back layer 40. The narrow first groove 66 is provided in connection with the bottom end of the dividing first groove 64 and reaches the bottom end of the back layer 40.

Next, a manufacturing procedure of the ultrasonic probe 3 of the third embodiment will be described focusing on differences from the ultrasonic probe 1 of the first embodiment. At the time of manufacturing the ultrasonic probe 3, the manufacturer laminates the unprocessed plate-shaped back layer 45, the unprocessed vibrator 15, and the unprocessed acoustic matching layer 25 shown in FIG. 3A as in the ultrasonic probe 1.

Subsequently, the manufacturer performs dicing from the unprocessed acoustic matching layer 25 to the unprocessed back layer 45 across the unprocessed vibrator 15 at a sub-dice pitch to alternately form the dividing first groove 64 and the second groove 70 to divide the unprocessed acoustic matching layer 25, the unprocessed vibrator 15, and the unprocessed hack layer 45. At this time, the manufacturing procedure is in a state before the stepped first grooves 62 for forming main dice divide the unprocessed back layer 45 (back layer 40).

Subsequently, the manufacturer dices the unprocessed back layer 45 from the bottoms of the stepped first grooves 62 disposed at a main dice pitch using a blade having a narrower width than a blade used to form the second grooves 70 and the stepped first grooves 62 through dicing to form the narrow first grooves 66 passing through the unprocessed back layer 45. By forming the narrow first grooves 66, the unprocessed back layer 45 is divided to form the back layer 40. Thereafter, the manufacturer provides the back material 50 on the back surface of the back layer 40 and provides the lens layer 30 on the upper surface of the acoustic matching layer 20. Through this procedure, the manufacturer manufactures the ultrasonic probe 3.

Since the second grooves 70 are provided in the ultrasonic probe 3 of the third embodiment as in the ultrasonic probe 1 of the first embodiment, the transverse vibration mode of the vibrator 10 can be suppressed. Since the penetration depth of the second grooves 70 is less than the width of the second grooves 70 in the ultrasonic probe 3, it is possible to reduce damage to the back layer 40 by providing the second grooves 70. It is possible to reduce an area (volume) in which the back layer 40 is diced by providing the stepped first grooves 62 in the ultrasonic probe 3. Accordingly, it is possible to reduce damage to the back layer 40.

Fourth Embodiment

Figure 8:
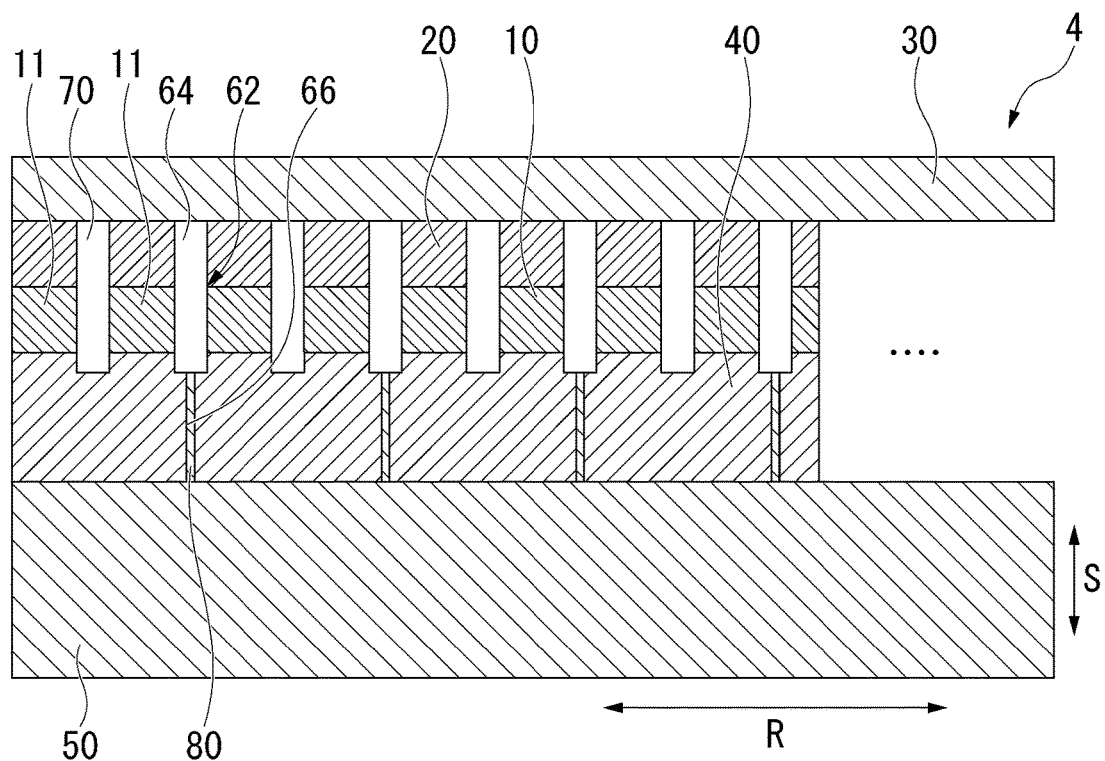
FIG. 8 is a cross-sectional view of an ultrasonic probe 4 of a fourth embodiment.

An ultrasonic probe 4 of a fourth embodiment will be described. FIG. 8 is a cross-sectional view of the ultrasonic probe 4 of the fourth embodiment. The ultrasonic probe 4 differs from that of the third embodiment in that a filler 80 is filled in the narrow first grooves 66. Other components are the same as those of the ultrasonic probe 3 of the third embodiment. The back layer 40 and the vibrator 10 of the ultrasonic probe 4 are attached to each other, for example, using an adhesive as in the ultrasonic probe 2 of the second embodiment. The adhesive is, for example, a liquid epoxy adhesive having an epoxy resin as a main ingredient. The filler 80 filled in the narrow first grooves 66 is the epoxy resin used as the adhesive that has flowed into the narrow first grooves 66 and solidified.

Next, in manufacture of the ultrasonic probe 4 of the fourth embodiment, the liquid adhesive is coated between the unprocessed back layer 45 and the unprocessed vibrator 15 when the unprocessed plate-shaped back layer 45, the unprocessed vibrator 15, and the unprocessed acoustic matching layer 25 shown in FIG. 3A are laminated. Subsequently, dicing is performed to form the second grooves 70 and the dividing first grooves 64 and the bottoms of the dividing first grooves 64 are diced to form the narrow first grooves 66 before the adhesive solidifies.

At the time of forming the narrow first grooves 66, the manufacturer applies a pressure between the unprocessed vibrator 15 and the unprocessed back layer 45 such that the adhesive flows into the narrow first grooves 66. Thereafter, the manufacturer solidifies the adhesive that has flowed into the first grooves 60 in the back layer 40 to fill the adhesive in the first grooves 60 as a filler in the back layer 40. After this, the ultrasonic probe 4 is manufactured through the same procedure as that of the third embodiment.

Since the second grooves 70 are provided in the ultrasonic probe 4 of the fourth embodiment as in the first embodiment, the transverse vibration mode of the vibrator 10 can be suppressed. Since the penetration depth of the second grooves 70 is less than the width of the second grooves 70 in the ultrasonic probe 4, it is possible to reduce damage to the back layer 40 by providing the second grooves 70. Since the filler is filled in the narrow first grooves 66 of the back layer 40 in the ultrasonic probe 4, it is possible to further reduce damage to the back layer 40. Further, manufacturing is facilitated because the adhesive coated between the unprocessed back layer 45 and the unprocessed vibrator 15 need not be finely adjusted.

Fifth Embodiment

Figure 9:
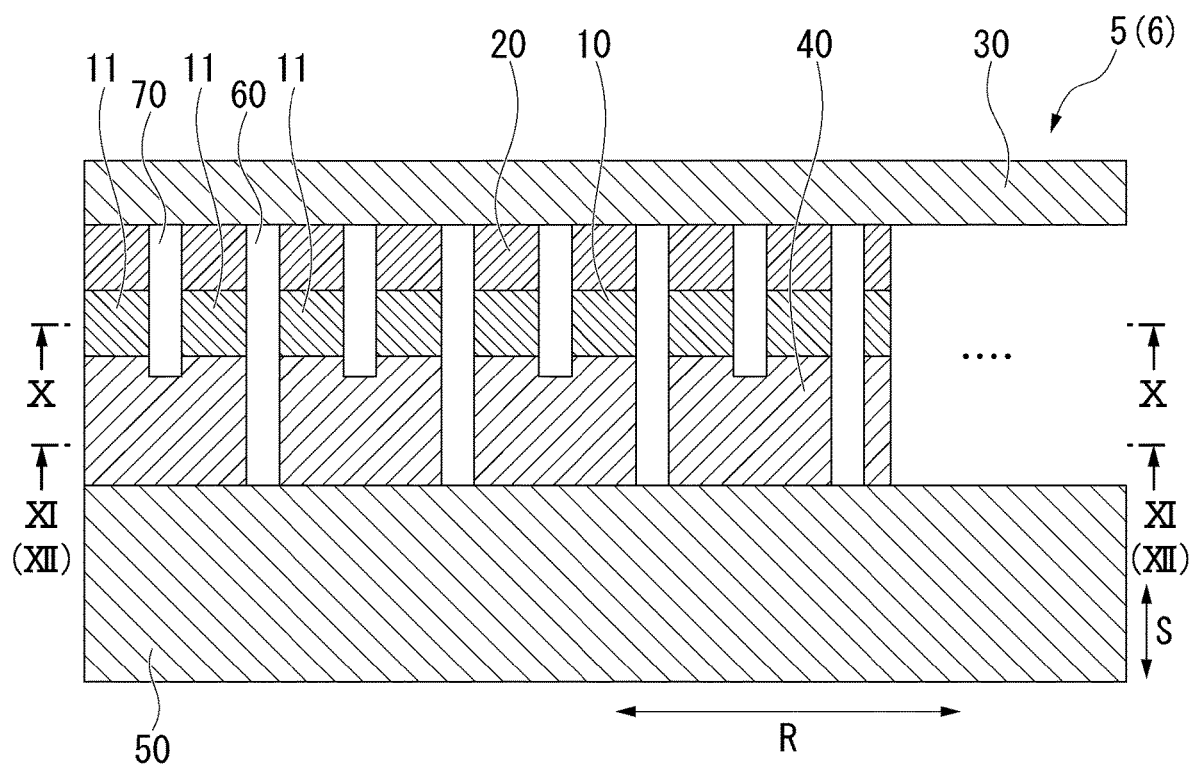
FIG. 9 is a cross-sectional view of an ultrasonic probe 5 of a fifth embodiment.
Figure 10:
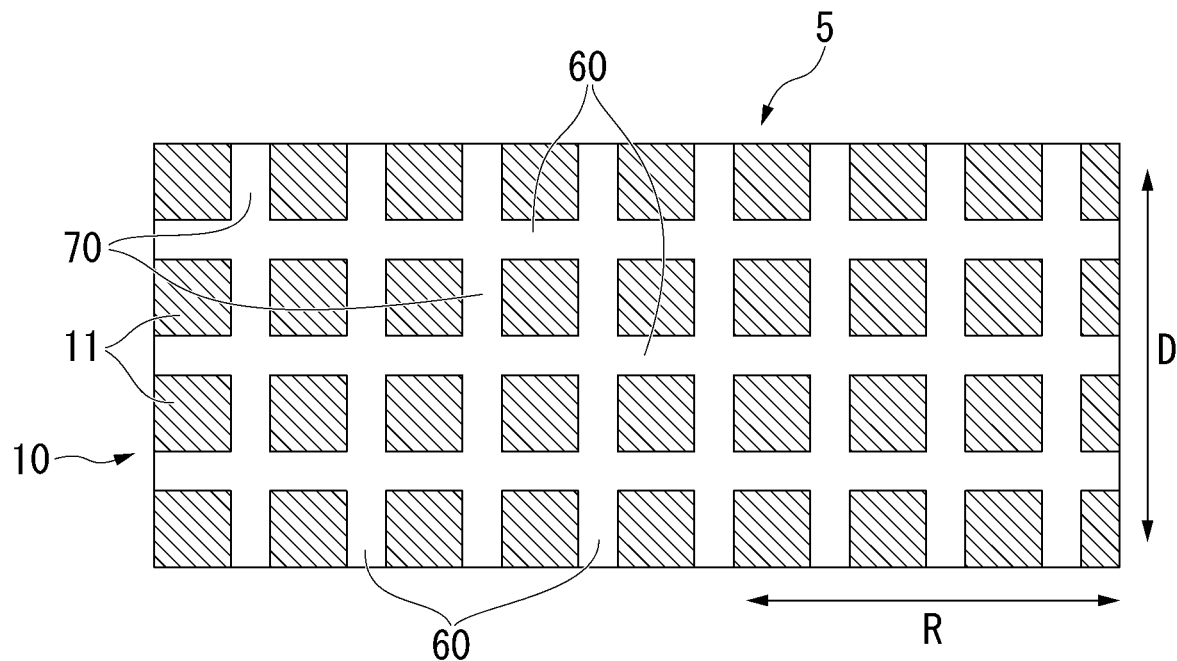
FIG. 10 is a cross-sectional view showing the ultrasonic probe 5 of the fifth embodiment along line X-X of FIG. 9.
Figure 11:
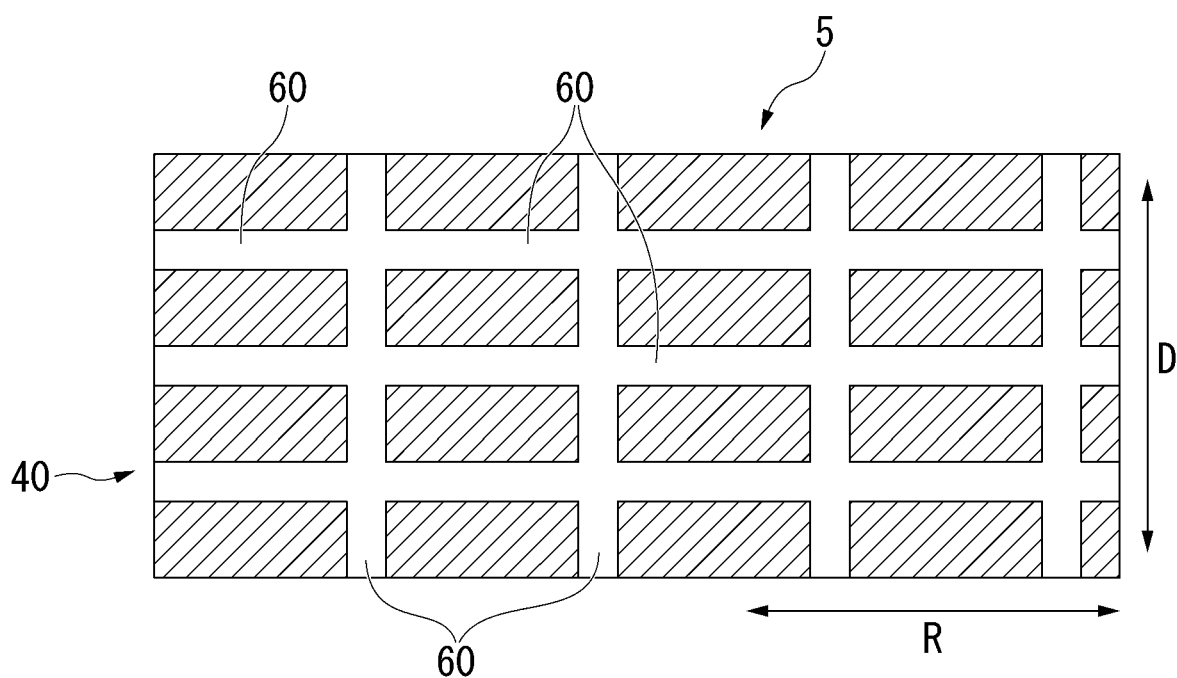
FIG. 11 is a cross-sectional view showing the ultrasonic probe 5 of the fifth embodiment along line XI-XI of FIG. 9.

An ultrasonic probe 5 of a fifth embodiment will be described. FIG. 9 is a cross-sectional view of the ultrasonic probe 5 of the fifth embodiment, FIG. 10 is a cross-sectional view showing the ultrasonic probe 5 of the fifth embodiment along line X-X of FIG. 9, and FIG. 11 is a cross-sectional view showing the ultrasonic probe 5 of the fifth embodiment along line XI-XI of FIG. 9. In the ultrasonic probe 5 of the fifth embodiment, the first grooves 60 provided in the ultrasonic probe 1 of the first embodiment are arranged in the first direction R and also arranged in a third direction D such as a depth direction perpendicular to both the first direction R and the second direction S.

A main dice pitch in the first direction R in the ultrasonic probe 5 is twice that of a main dice pitch in the third direction D. Since the main dice pitch in the first direction R is twice that of a sub-dice pitch in the first direction R, the main dice pitch in the third direction D is the same as the sub-dice pitch in the first direction R. In the vibrating elements 11, two sub-dice are disposed in the first direction R for one main dice.

In the ultrasonic probe 5 of the fifth embodiment, the vibrating elements 11 are arranged two-dimensionally including the third direction D as well as a one-dimensional direction of the first direction R. Accordingly, it is possible to perform ultrasonic diagnosis in a wider range through one operation as compared to an aspect in which the vibrating elements 11 are arranged only in the one-dimensional direction. When this ultrasonic diagnosis is performed in a wide range, it is possible to suppress the transverse vibration mode of the vibrator 10 and to reduce damage to the back layer 40 by providing the second grooves 70.

Sixth Embodiment

Figure 12:
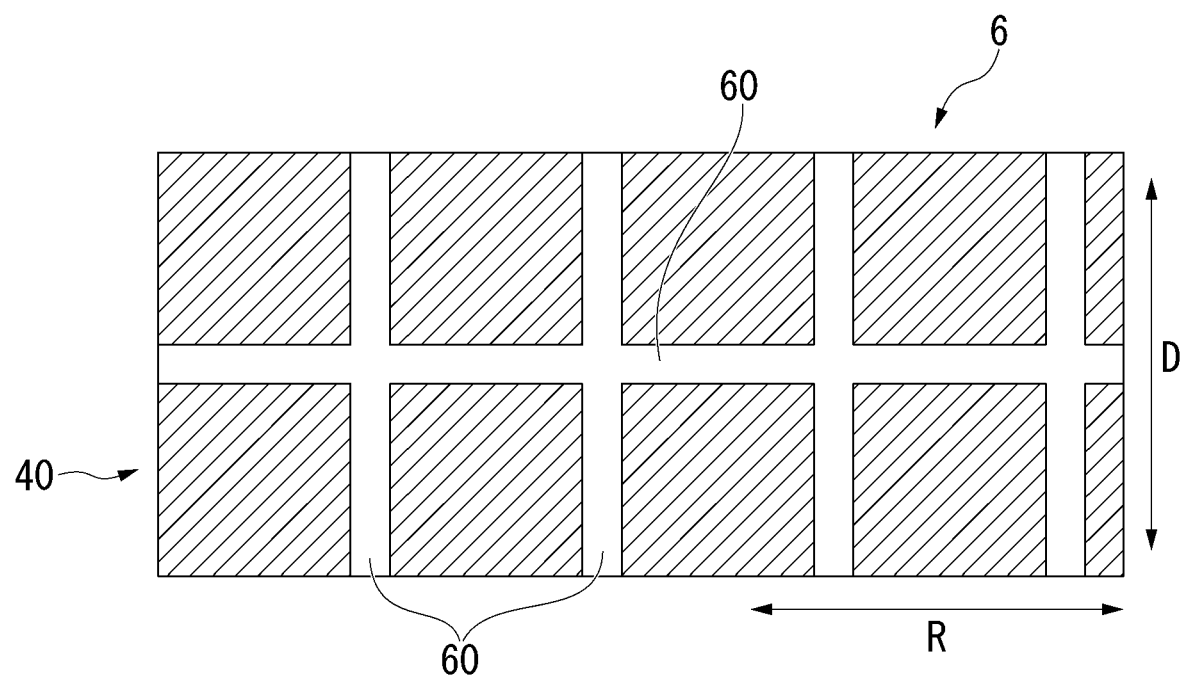
FIG. 12 is a cross-sectional view showing an ultrasonic probe 6 of a sixth embodiment along line XII-XII of FIG. 9.

An ultrasonic probe 6 of a sixth embodiment will be described. The ultrasonic probe 6 of the sixth embodiment differs from the ultrasonic probe 5 of the fifth embodiment with respect to the number of vibrating elements 11 arranged in the third direction. A cross-sectional view of the ultrasonic probe 6 of the sixth embodiment and a cross-sectional view thereof along line X-X are the same as the cross-sectional view of the ultrasonic probe 5 of the fifth embodiment and the cross-sectional view thereof along line X-X. FIG. 12 is a cross-sectional view of the ultrasonic probe 6 of the sixth embodiment along line XII-XII of FIG. 9.

A main dice pitch in the first direction R in the ultrasonic probe 6 of the sixth embodiment is the same as a main dice pitch in the third direction D, and the main dice pitch is twice that of a sub-dice pitch in both the first direction R and the third direction D. Four sub-dice are arranged for one main dice with two arranged in the first direction R and two arranged in the third direction D.

As can be seen in the fifth embodiment and the sixth embodiment, when the vibrating elements 11 are arranged in two-dimensional directions of the first direction R and the third direction D, for example, in the vibrator 10, the number of vibrating elements 11 arranged in the first direction R may be identical to or different from the number of vibrating elements 11 arranged in the third direction D. The relationship between the sub-dice pitch and the main dice pitch in the vibrating elements 11 arranged in the first direction R may be identical to or different from that in the vibrating elements 11 arranged in the third direction D.

According to at least one of the above-described embodiments, the vibrator including a plurality of vibrating elements arranged in the first direction, the acoustic matching layer formed on the living body side of the vibrator, and the back layer formed on the back side of the vibrator are provided, the plurality of vibrating elements are formed by being divided by the first grooves passing through the vibrator and the back layer, the second grooves passing through the vibrating elements and penetrating into the back layer are provided in each of the vibrating elements, and the penetration depth of the second grooves in the second direction in the back layer is less than the width of the second grooves in the first direction in the vibrating elements, and thus it is possible to reduce damage to the back layer while suppressing the transverse vibration mode of the vibrator.

Although several embodiments have been described, these embodiments have been suggested as examples and are not intended to limit the scope of the invention. These embodiments can be implemented in various other forms and various omissions, substitutions and modifications are possible without departing from essential characteristics of the invention. These embodiments and modifications thereof are included in the scope and essential characteristics of the invention and also included in the invention disclosed in the claims and the equivalents thereof.

What is claimed is:

1. An ultrasonic probe, comprising:
a vibrator including a plurality of vibrating elements arranged in a first direction;
an acoustic matching layer formed on a living body side of the vibrator; and
a back layer formed on a back side of the vibrator opposite the living body side, the back layer being formed on one surface of the vibrator
wherein the plurality of vibrating elements are formed by being divided by first grooves passing entirely through both the vibrator and the back layer,
second grooves passing through the plurality of vibrating elements and penetrating into the back layer are provided in each of the plurality of vibrating elements, and
a penetration depth of the second grooves in a second direction in the back layer is less than a width of the second grooves in the first direction in the plurality of vibrating elements.

2. The ultrasonic probe according to claim 1, wherein the penetration depth of the second grooves in the second direction in the back layer is 0.8 times or less the width of the second grooves in the first direction in the plurality of vibrating elements.

3. The ultrasonic probe according to claim 1, wherein a filler is filled in the first grooves in the back layer.

4. The ultrasonic probe according to claim 3, wherein the filler is an epoxy resin.

5. The ultrasonic probe according to claim 1, wherein a width of at least a part of the first grooves in the first direction in the back layer is less than a width of the first grooves in the first direction in the vibrator.

6. The ultrasonic probe according to claim 1, wherein the plurality of vibrating elements are arranged in the first direction and a third direction perpendicular to both the first direction and the second direction.

* * * * *